United States Patent [19]

Chikama et al.

[11] Patent Number: 5,178,129
[45] Date of Patent: Jan. 12, 1993

[54] METHOD OF PRODUCING BENDING DEVICE

[75] Inventors: Toshio Chikama, Tokyo; Tokusaburo Yoshihashi, Chiba, both of Japan

[73] Assignee: Kabushiki Kaisha Machida Seisakusho, Tokyo, Japan

[21] Appl. No.: 623,691

[22] Filed: Dec. 7, 1990

[30] Foreign Application Priority Data

Dec. 28, 1989 [JP] Japan .................. 1-340450

[51] Int. Cl.$^5$ .............................................. A61B 1/00
[52] U.S. Cl. .......................................... 128/4; 138/120
[58] Field of Search .................... 128/4, 898; 138/120

[56] References Cited

U.S. PATENT DOCUMENTS 3,060,972 10/1962 Sheldon .
4,432,349 2/1984 Oshiro .
4,834,069 5/1989 Umeda .

FOREIGN PATENT DOCUMENTS 3534479 7/1986 Denmark .
3704815 8/1987 Denmark .
204031 11/1983 Fed. Rep. of Germany .......... 128/4
10605 1/1980 Japan .
5501 3/1981 Japan .
157302 10/1982 Japan .
166137 10/1982 Japan .
108027 6/1985 Japan .

Primary Examiner—Robert Bahr
Assistant Examiner—Karen Ann Richard
Attorney, Agent, or Firm—Fish & Richardson

[57] ABSTRACT

A method of producing a bending device is disclosed. There are provided a plurality of elongated arcuate assemblies each formed by pivotally connecting a row of arcuate members to one another by connecting elements, the arcuate assembly extending in a direction of the widths of the arcuate members. Subsequently, the plurality of arcuate assemblies are connected together in such a manner that ends of corresponding ones of the arcuate members of the arcuate assemblies are fixed together to form the row of joint rings, thereby forming the ring assembly.

15 Claims, 6 Drawing Sheets

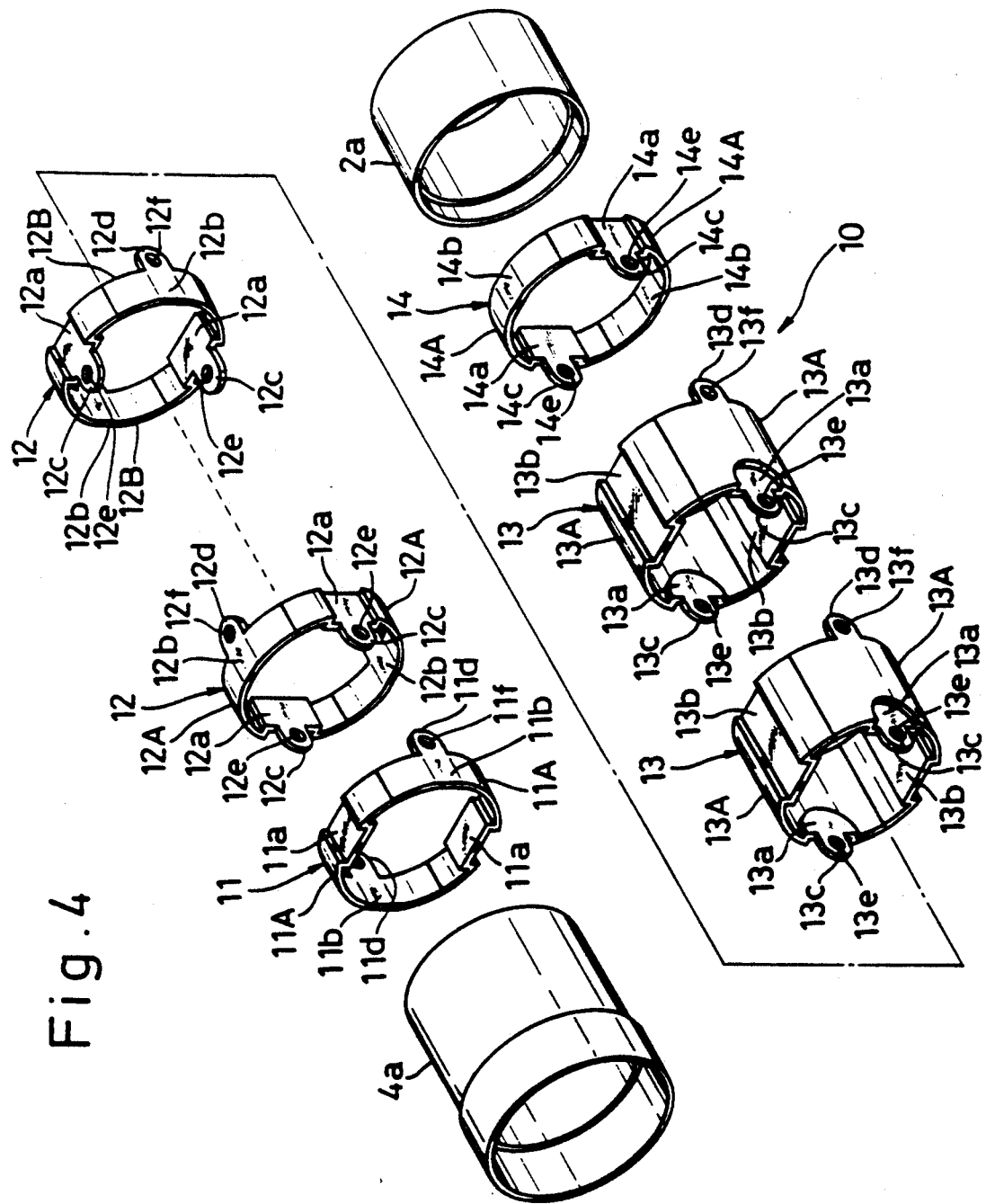

METHOD OF PRODUCING BENDING DEVICE

BACKGROUND OF THE INVENTION

This invention relates to a method of producing a bending device for use in an endoscope or the like.

Japanese Laid-Open (Kokai) Utility Model Application No. 157302/82 discloses a bending device for use in an endoscope which device is bendable in four directions. This bending device comprises a ring assembly, and four operating wires.

The ring assembly comprises a number of joint rings arranged in a row and pivotally connected to one another. More specifically, each of the joint rings has a pair of first diametrically-opposite connecting portions, and a pair of second diametrically-opposite connecting portions circumferentially spaced 90° from the first connecting portions. The first connecting portions and the second connecting portions extend in opposite directions along the axis of the ring assembly, that is, in the direction of the width of the joint ring. For example, the first connecting portions extend forwardly while the second connecting portions extend rearwardly. A through hole is formed through each of the connecting portions.

The connection between the adjacent joint rings will now be described. The pair of second connecting portions of the forward joint ring are pivotally connected respectively to the pair of first connecting portions of the rearward joint ring by respective rivets passing through the through holes of the connecting portions.

The joint rings are connected together in the following manner. The joint rings are fitted in a row on an elongated support base of a circular cross-section supported in a cantilever manner. The second connecting portions of a forward one of any two adjacent joint rings are superposed respectively on the first connecting portions of the rearward joint ring, and the rivets are passed through the respective mating through holes of these connecting portions. The rivets are deformed by a punch disposed outside the joint rings, thereby pivotally connecting the first and second connecting portions together.

Since the punch is disposed outside the joint rings, the head of each rivet is disposed inside the joint rings, with the distal end of the stem of the rivet projected outwardly from the outer periphery of the joint ring, and in this condition the rivet must be deformed. This invites the following disadvantages. The rivet must be first disposed inside the joint ring, and then the stem of the rivet must be passed through the through holes of the mating connecting portions. Thus, the position of the rivet can not be confirmed with the eyes, and therefore the operability is not good. Particularly when forming the ring assembly of a small diameter, the operability is extremely bad.

In addition, since the support base is of the cantilever type, it has a low strength and can not satisfactorily receive the force applied from the punch. This results in problems that the deformation of the rivet is incomplete and that much time is required for deforming the rivet. These problems are serious particularly when forming the ring assembly of a small diameter.

With respect to other prior art, Japanese Laid-Open Utility Model Application No. 5501/81 discloses a technique in which adjacent joint rings are connected together by stepped rivets. Although each rivet is fixed to an outward one of the mating connecting portions, the rivet is positively angularly movable relative to the inward connecting portions.

Japanese Laid-Open Utility Model Application No. 108027/85 discloses a technique in which a connecting member having a stem is fixed by a laser or the like to an outward one of mating connecting portions of adjacent joint rings.

Japanese Laid-Open Utility Model Application No. 10605/80 discloses a bending device comprising a spring and a plurality of rings for keeping the pitch of the spring constant. Each ring is composed of a pair of arcuate members of a semi-circular shape fixed together at their ends. However, the rings are not connected to one another, but are merely held in contact with one another. Thus, the rings do not constitute a ring assembly.

Japanese Laid-Open Patent Application No. 166137/82 discloses a bending device in which each pair of arcuate members of a semi-circular shape are bent at their opposite ends to form insertion portions, and wires are passed through the insertion portions to thereby connect the pair of arcuate members to form a ring. The adjacent rings are connected together by these wires, so that the rings constitute a ring assembly. This ring assembly is low in strength.

SUMMARY OF THE INVENTION

With the above problems of the prior art in view, it is an object of this invention to provide a method of producing a bending device in which the operability with respect to the formation of a ring assembly is improved.

According to the present invention, there is provided a method of producing a bending device comprising an elongated ring assembly and operating wire means for bending the ring assembly, the ring assembly comprising a row of joint rings, and connecting elements pivotally connecting adjacent ones of the joint rings, a distal end of the operating wire means being substantially fixed to a front end of the ring assembly, a proximal end of the operating wire means being adapted to receive an operating force, the method comprising the steps of:
(a) providing a plurality of elongated arcuate assemblies each formed by pivotally connecting a row of arcuate members to one another by the connecting elements, the arcuate assembly extending in a direction of the widths of the arcuate members; and
(b) connecting the plurality of arcuate assemblies together in such a manner that ends of corresponding ones of the arcuate members of the arcuate assemblies are fixed together to form the row of joint rings, thereby forming the ring assembly.

BRIEF DESCRIPTION OF THE DRAWINGS

FIG. 4 is an exploded perspective view of the bending device, with rivets omitted;

DESCRIPTION OF THE PREFERRED EMBODIMENTS OF THE INVENTION

One preferred embodiment of the invention will now be described with reference to FIGS. 1 to 8.

Figure 1:
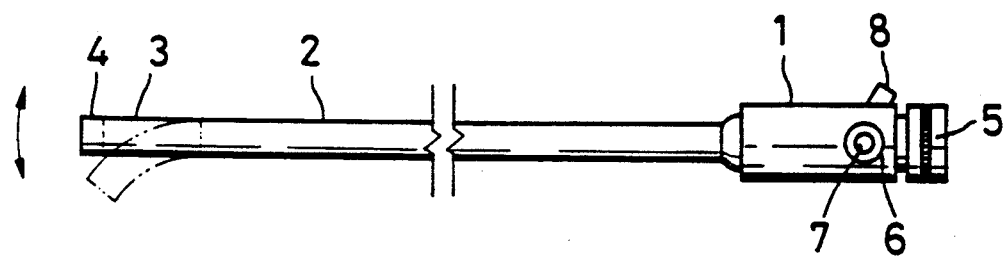
FIG. 1 is a side-elevational view of an endoscope incorporating a bending device according to the present invention.

An endoscope shown in FIG. 1 comprises a hollow body 1, an insertion portion 2 extending from the front end of the body 1, a bending portion (bending device) 3 extending from the distal end of the insertion portion 2, and a rigid portion 4 provided at the distal end of the bending portion 3. Each of the insertion portion 2 and the bending portion 3 has a tubular shape, and is so flexible as to be bent.

An ocular tube 5 is provided at the proximal end of the body 1, and manipulation dials 6 and 7 and a forceps inlet portion 8 are provided on the peripheral wall of the body 1. A cable (not shown) is connected at one end to the peripheral wall of the body 1, and a connector (not shown) to be connected to a light source device is connected to the other end of this cable.

Figure 2:
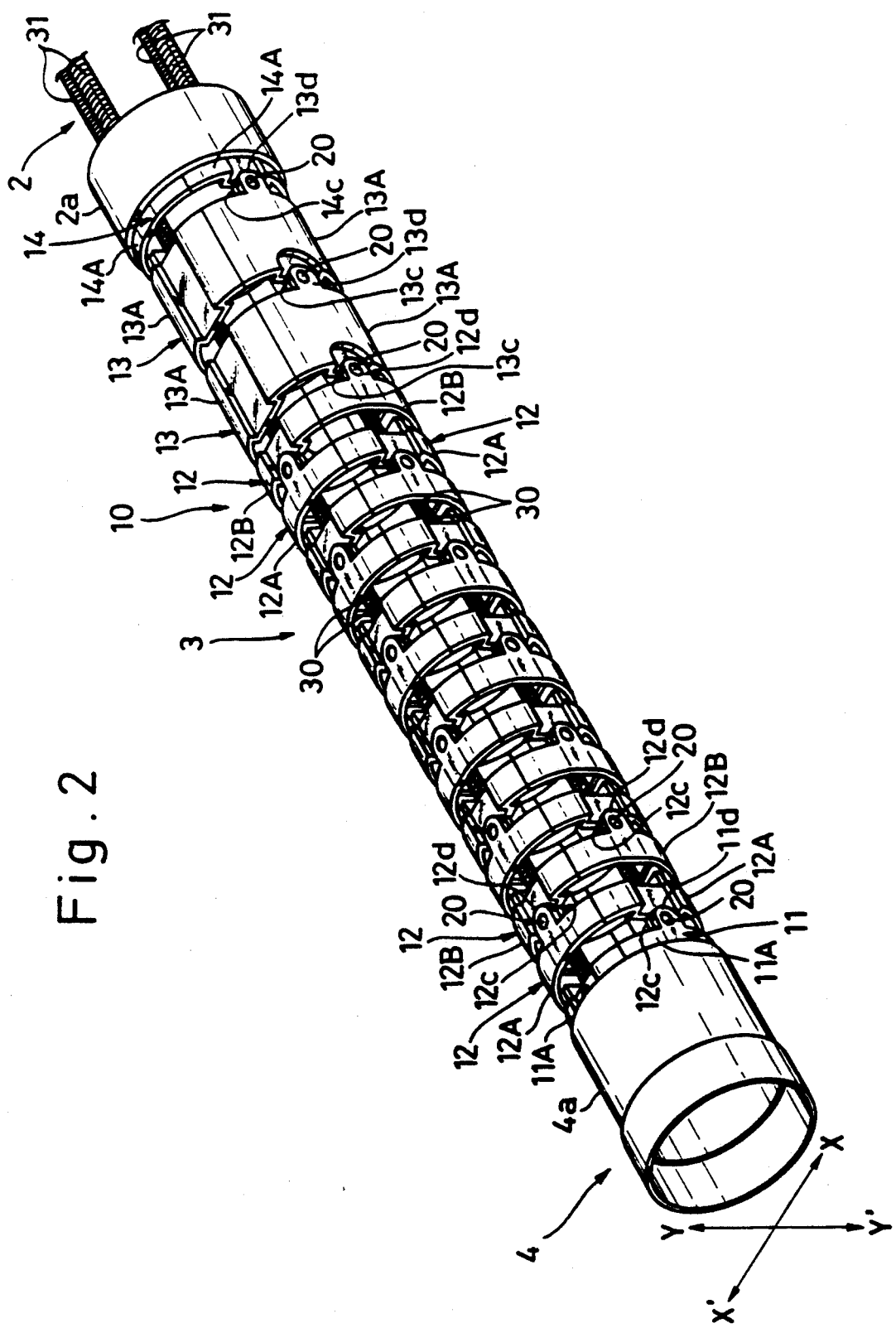
FIG. 2 is a perspective view of the bending device.

As shown in FIG. 2, the rigid portion 4 includes a tubular frame 4a. A support member of a circular cross-section is fixedly received in the front end portion of the frame 4a. An inspection window, an illumination window, a forceps outlet and etc., are provided at this support member. The ocular tube 5 is optically connected to the inspection window via an image transmitting optical system (not shown) including an optical fiber bundle passing through the body 1, the insertion portion 2 and the bending portion 3. With this arrangement, the inspection can be made from the ocular tube 5. Illumination light from the light source device is supplied to the illumination window via an optical fiber bundle (not shown) passing through the above connector, the above cable, the body 1, the insertion portion 2 and the bending portion 3. The forceps outlet is connected to the forceps inlet portion 8 via a guide tube (not shown) passing through the body 1, the insertion portion 2 and the bending portion 3.

The insertion portion 2 comprises a coil made of a strip, a braid fitted on this coil, and a resin tube fitted on this braid. The strip coil is connected at its front end to an inner peripheral surface of a rear end portion of a connecting tube 2a (FIG. 2).

As shown in FIG. 2, the bending portion 3 includes a ring assembly 10. A braid, which is softer than the braid fitted on the insertion portion 2, is fitted on the outer periphery of the ring assembly 10, and another resin tube, which is softer than the resin tube on the insertion portion 2, is fitted on the braid.

The ring assembly 10 will now be described in detail. As shown in FIGS. 2 and 4, the ring assembly 10 comprises a front-end joint ring 11, a plurality of (twelve in this embodiment) main joint rings 12, two auxiliary joint rings 13, and a rear-end joint ring 14. These joint rings 11 to 14 are arranged in a row in the above-mentioned order in the direction of the width of these joint rings.

Each main joint ring 12 has a substantially uniform width over the entire circumference thereof, and has a pair of diametrically-opposite first flat portions 12a and a pair of diametrically-opposite second flat portions 12b. The first flat portions 12a are circumferentially spaced 90° from the second flat portions 12b. Each of the first flat portion 12a is offset or recessed radially inwardly from the remainder of the main joint ring 12 by an amount equal to the thickness of the main joint ring 12. A first connecting portion 12c extends forwardly from each of the first flat portions 12a in the direction of the width of the main joint ring 12, that is, along the axis of the ring assembly 10. A second connecting portion 12d extends rearwardly from each of the second flat portions 12b in a direction opposite to the direction of extending of each first connecting portion 12c. A through hole 12e is formed through each first connecting portion 12c, and a through hole 12f is formed through each second connecting portion 12d.

The front-end joint ring 11 is similar to the main joint ring 12 in that the front-end joint ring 11 has a pair of first flat portions 11a, a pair of second flat portions 11b and a pair of rearwardly-extending connecting portions 11d each having a through hole 11f, but the front-end joint ring 11 has no forwardly-extending connecting portion.

The rear-end joint ring 14 is similar to the main joint ring 12 in that the rear-end joint ring 14 has a pair of first flat portions 14a, a pair of second flat portions 14b and a pair of forwardly-extending connecting portions 14c each having a through hole 14e, but the rear-end joint ring 14 has no rearwardly-extending connecting portion.

Each of the auxiliary joint rings 13 is greater in width than the main joint ring 12, and has a pair of diametrically-opposite first flat portions 13a formed at its front end portion and offset radially inwardly by an amount equal to the thickness of the auxiliary joint ring 13. A pair of first connecting portions 13c each having a through hole 13e extend forwardly from the pair of first flat portions 13a, respectively. A pair of diametrically-opposite second connecting portions 13d each having a through hole 13f extend rearwardly from the rear end of the auxiliary joint ring 13. The pair of second connecting portions 13d are disposed respectively in registry with the pair of first connecting portions 13c in the axial direction of the auxiliary joint ring 13. The auxiliary joint ring 13 further has a pair of diametrically-opposite second flat portions 13b offset radially inwardly by an amount equal to the thickness of the auxiliary joint ring 13, and the second flat portions 13b are circumferentially spaced 90° from the connecting portions 13c and the 13d.

Figure 3:
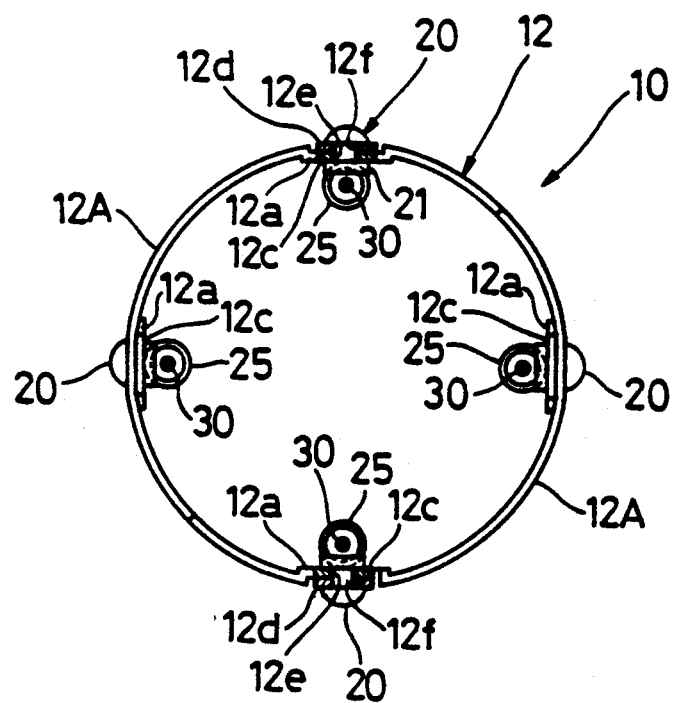
FIG. 3 is a transverse cross-sectional view of the bending device.

Any adjacent two of the main joint rings 12 are circumferentially displaced 90° from each other, and are pivotally connected together. As best shown in FIG. 3, each second connecting portion 12d of the forward one of the adjacent main joint rings 12 overlaps the corresponding first connecting portion 12c of the rearward main joint ring 12 in such a manner that the first connecting portion 12c is disposed inwardly of the second connecting portion 12d. In this overlapping condition, the through holes of these first and second connecting portions 12c and 12d are aligned with each other. The overlapping connecting portions 12c and 12d are pivotally connected together by a rivet 20 passing through the aligned through holes 12e and 12f.

Similarly, the connecting portions 11d of the front-end joint ring 11 are pivotally connected respectively to the first connecting portions 12c of a forefront (extreme front) one of the main joint rings 12 by respective rivets 20. The first connecting portions 13c of the forward auxiliary joint ring 13 are pivotally connected respectively to the second connecting portions 12d of an extreme rear one of the main joint rings 12 by respective rivets 20. The first connecting portions 13c of the rearward auxiliary joint ring 13 are pivotally connected respectively to the second connecting portions 13d of the forward auxiliary joint ring 13 by respective rivets 20. The connecting portions 14c of the rear-end joint ring 14 are pivotally connected respectively to the second connecting portions 13d of the rearward auxiliary joint ring 13 by respective rivets 20.

The ring assembly 10 of the above construction is bendable in X—X' direction and in Y—Y' direction (FIG. 2).

The front-end joint ring 11 of the ring assembly 10 is fixedly secured to the inner peripheral surface of the rear end portion of the frame 4a of the rigid portion 4 by brazing or the like. The rear-end joint ring 14 of the ring assembly 10 is fixedly secured to the inner peripheral surface of the front end portion of the connecting tube 2a by brazing or the like. The rear-end joint ring 14 is connected to the front end of the strip coil of the insertion portion 2 via the connecting tube 2a.

As shown in FIG. 3, guide tubes 25 are fixedly secured respectively to the inner surfaces of the flat portions 12a of each main joint rings 12 by brazing or the like, and similar guide tubes 25 are fixedly secured to the inner surfaces of the flat portions 13a of each auxiliary joint tubes 13 by brazing or the like. Therefore, there are provided four rows of guide tubes 25 arranged along the axis of the ring assembly 10. An operating wire 30 is passed through each row of guide tubes 25. The four operating wires 30 are circumferentially spaced 90° from one another.

The front ends of the operating wires 30 are fixedly secured to the tubular frame 4a of the rigid portion 4 or a member fixed to the frame 4a, and the points of fixing of these front ends are circumferentially spaced 90° from one another. The operating wires 30 are passed through the insertion portion 2, and extend into the body 1. One pair of diametrically-opposite operating wires 30 are connected at their rear ends to a pulley (not shown) adapted to be angularly moved by the manipulation dial 6. The other pair of diametrically-opposite operating wires 30 are connected at their rear ends to a pulley (not shown) adapted to be angularly moved by the manipulation dial 7. At the insertion portion 2, the four operating wires 30 are received respectively in four guide coils 31 (FIG. 2). The front ends of the guide coils 31 are fixedly secured to the inner peripheral surface of the connecting tube 2a or the inner peripheral surface of the rear end joint ring 14, and the rear ends thereof are fixed within the body 1.

Therefore, when one manipulation dial 6 is angularly moved, one of the pair of operating wires 30 is pulled whereas the other is loosened. Therefore, the ring assembly 10 and hence the bending portion 3 are bent in either of the directions X and X'. Also, when the other manipulation dial 7 is angularly moved, one of the other pair of operating wires 30 is pulled whereas the other is loosened. Therefore, the ring assembly 10 and hence the bending portion 3 are bent in either of the directions Y and Y'.

The basic construction and operation of the above bending portion are similar to those of a conventional device of the ordinary type. Features of the present invention will now be described. As shown in FIGS. 2 to 4, the front-end joint ring 11 of the ring assembly 10 comprises a pair of identical arcuate members 11A of a semi-circular shape. Similarly, each of the odd-numbered main joint rings 12 counting from the front end of the ring assembly 10 comprising a pair of identical arcuate members 12A of a semi-circular shape. Each of the even-numbered main joint rings 12 comprises a pair of identical arcuate members 12B of a semi-circular shape. The arcuate member 12A is symmetrical to the arcuate member 12B, that is, one is a mirror image of the other. Similarly, each auxiliary joint ring 13 comprises a pair of identical arcuate members 13A of a semi-circular shape, and the rear-end joint ring 14 comprises a pair of identical arcuate members 14A of a semi-circular shape.

The arcuate member 11A has the connecting portion 11d circumferentially spaced 45° from one end thereof. Each of the arcuate members 12A and 12B has the first connecting portion 12c circumferentially spaced 45° from one end thereof, and has the second connecting portion 12d circumferentially spaced 45° from the other end. Each arcuate member 13A has the first and second connecting portions 13c and 13d circumferentially spaced 45° from one end thereof. The arcuate member 14A has the connecting portion 14c circumferentially spaced 45° from one end thereof.

A method of forming the above ring assembly 10 will now be described with reference to FIGS. 5 to 8. Elongated plates are stamped from a metal sheet, and then are formed by pressing into an arcuate shape to provide the arcuate members 11A, 12A, 12B, 13A and 14A, respectively.

Figure 5:
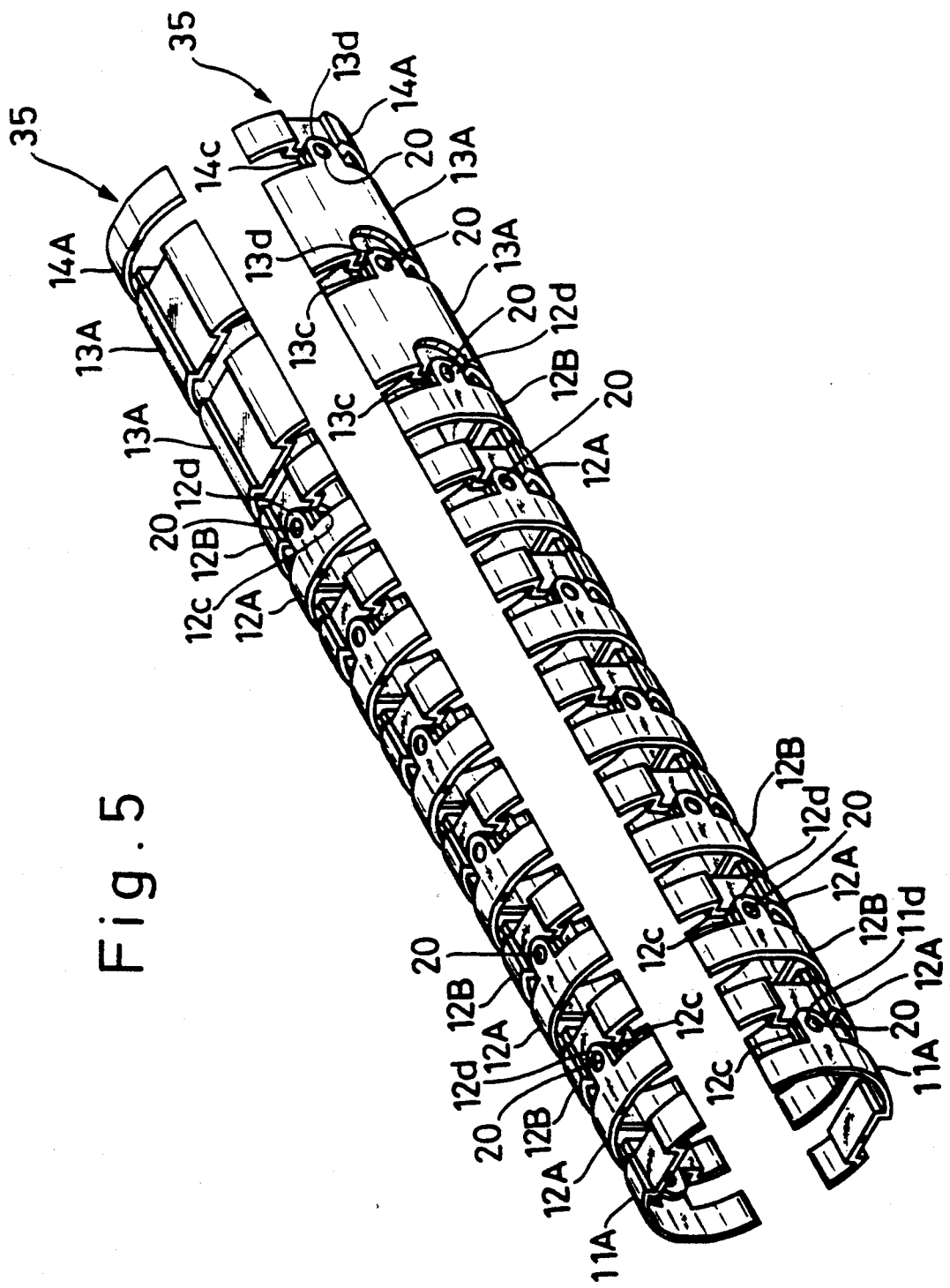
FIG. 5 is a perspective view of a pair of arcuate assemblies obtained during the process of producing the bending device.
Figure 6:
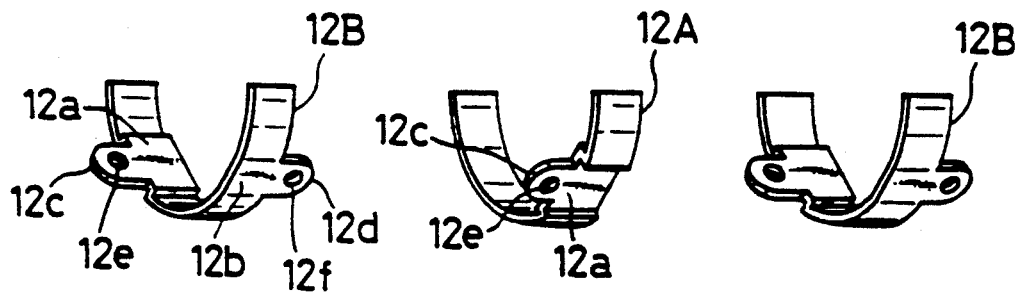
FIG. 6 is an exploded perspective view of a portion of the arcuate assembly.

Then, the arcuate members 11A to 14A are pivotally connected to one another by the rivets 20 to form a pair of arcuate assemblies 35 shown in FIG. 5. More specifically, the arcuate members 12A and 12B are alternately connected to the arcuate member 11A, and further the two arcuate members 13A and the arcuate member 14A are connected in this order, thereby forming each arcuate assembly 35.

Figure 7:
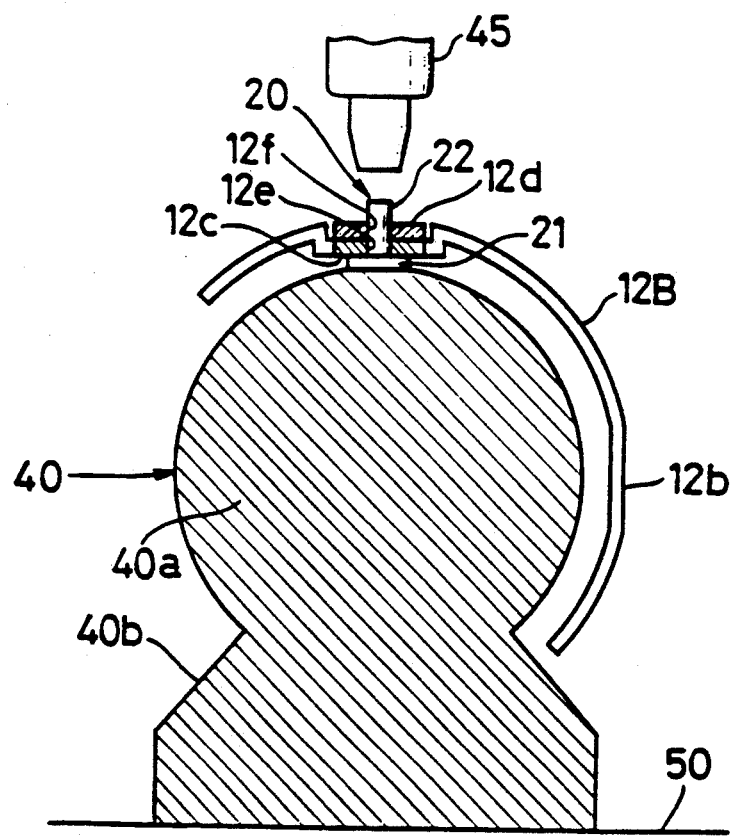
FIG. 7 is a cross-sectional view showing the step of connecting arcuate members by a rivet so as to form the arcuate assembly.

This connecting operation will now be described with respect to the arcuate members 12A and 12B, as shown in FIG. 7. The second connecting portion 12d of the arcuate member 12A is caused to overlap the first connecting portion 12c of the arcuate member 12B, with the through holes 12e and 12f aligned with each other, in such a manner that the second connecting portion 12d is disposed outwardly of the first connecting portion 12c. Heads 21 of the rivets 20 are disposed inside the arcuate members 12A and 12B, and in this condition a stem 22 of this rivet 20 is passed through the aligned through holes 12e and 12f, so that the distal end of the stem 22 is projected outwardly of the arcuate members 12A and 12B. The head 21 of the rivet 20 rests on a support base 40, and in this condition a punch 45 disposed above the support base 40 is moved downward to crush the distal end portion of the rivet 20 to thereby connect the connecting portions 12c and 12d together, thus connecting the arcuate members 12A and 12B together.

In the above connecting operation, while confirming the alignment of the two through holes 12e and 12f with each other, the stem 22 of the rivet 20 is passed through these through holes. Alternatively, the rivet 20 is first kept passed through the through hole 12e of the first connecting portion 12c, and then the rivet 20 is passed through the through hole 12f of the second connecting portion 12d. Any way, since the arcuate members 12A and 12B are of a semi-circular shape, the through holes 12e and 12f and the rivet 20 can be seen with the eyes, and therefore the passing of the rivet 20 can be made easily.

Also, since the arcuate members 12A and 12B are of a half-ring shape, the support base 40 is not limited by the radius of curvature of the arcuate members 12A and 12B, and can have a large cross-sectional area. For example, as shown in FIG. 7, the support base 40 has a round portion 40a and a reinforcement portion 40b formed on the lower end of the round portion 40a. The support base 40 is not of the cantilever type, and can be placed on a table 50 or a floor. As a result, the support base 40 can receive a large force applied from the punch 45, and therefore the rivet 20 can be sufficiently deformed by the large force from the punch 45. This not only reduces the time required for deforming the rivet 20, but also enables a positive deformation of the rivet 20.

The connection between the arcuate members 11A and 12A, the connection between the arcuate members 12B and 13A, the connection between the arcuate members 13A, and the connection between the arcuate members 13A and 14A are carried out in a similar manner as described above.

Then, the guide tubes 25 and etc., are fixedly secured to the flat portions 12a and 13a of the arcuate members 12A, 12B and 13A by brazing or the like.

Figure 8:
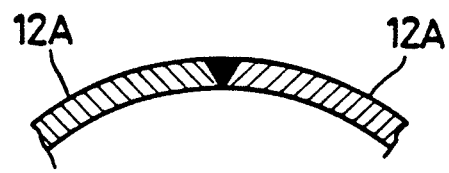
FIG. 8 is a fragmentary cross-sectional view showing the step of fixing the mating arcuate members of the pair of arcuate assemblies at their ends.

Then, the arcuate members 11A and 11A of the pair of the arcuate assembly 35 and 35, as well as the corresponding arcuate members 12A and 12A, the corresponding arcuate members 12B and 12B, the corresponding arcuate members 13A and 13A and the arcuate members 14A and 14A, are fixedly connected together at their ends. This will now be described, for example, with reference to the corresponding arcuate members 12A and 12A. As shown in FIG. 8, the mating ends of the arcuate members 12A and 12A are abutted against each other, and then the thus abutted ends are brazed.

In the above embodiment, the guide tubes 25 may be fixed to the arcuate members 12A, 12B and 13A before the arcuate assembly 35 is formed, in which case the support base 40 has recesses for receiving the guide tubes 25.

Figure 9:
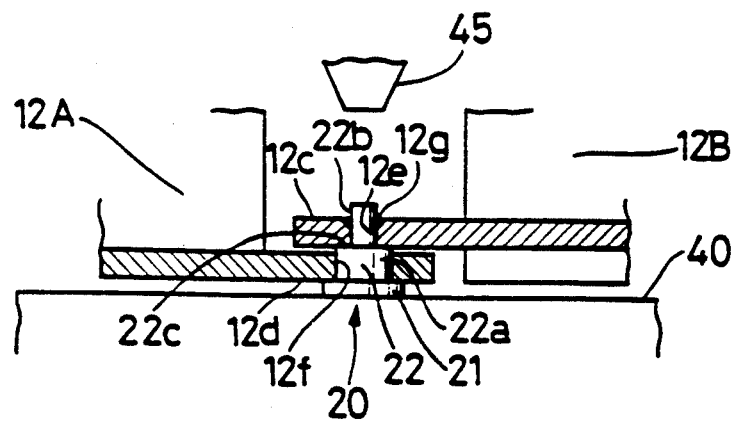
FIGS. 9 and 10 are cross-sectional views respectively showing modified steps of pivotally connecting the arcuate members so as to form the arcuate assembly.

FIG. 9 shows a modified rivet-deforming method. A stem 22 of a rivet 20 has a greater-diameter portion 22a close to a head 21, and a smaller-diameter portion 22b close to the distal end of the rivet 20. A step or shoulder 22c is formed between the greater-diameter and smaller-diameter portions 22a and 22b. A through hole 12e of the first connecting portion 12c disposed inwardly of the second connecting portion 12d is smaller in diameter than a through hole 12f of the second connecting portion 12d. The inner end of the through hole 12e is enlarged to form a counterbore 12g. The rivet 20 is passed through the through holes 12e and 12f of the connecting portions 12c and 12d from outside the arcuate members 12A and 12B. In this condition, the greater-diameter portion 22a of the stem 22 of the rivet 20 is passed through the through hole 12f, and the smaller-diameter portion 22b is passed through the through hole 12e, and the distal end portion of the smaller-diameter portion 22 is projected from the inwardly-disposed first connecting portion 12c. Then, the head 21 of the rivet 20 is held against a support base 40, with the ends of the arcuate members 12A and 12B directed upwardly, and in this condition the punch 45 is moved downward to crush the distal end portion of the smaller-diameter portion 22b, thus deforming the rivet 20.

The embodiment of FIG. 9 has the following advantages. When the thickness of the outwardly-disposed second connecting portion 12d is smaller than the length of the greater-diameter portion 22a, the deforming force applied from the punch 45 does not act on the greater-diameter portion 22a. Therefore, even when the deforming force of the punch 45 is made large, the pivotal movement between the greater-diameter portion 22a and the second connecting portion 12d is ensured. Since the deforming force of the punch 45 can be thus increased, the inwardly-disposed first connecting portion 12c can be firmly clamped between the the step 22c of the rivet 20 and the crushed distal end portion of the rivet 20, without any play or gap. Therefore, the rivet 20 is substantially fixed relative to the first connecting portion 12c. As a result, the rivet 20 is prevented from axially moving relative to the first connecting portion 12c. The distal end portion of the rivet 20 will not move inwardly relative to the first connecting portion 12c, and the crushed portion of the distal end portion of the rivet 20 is received in the counterbore 12g. With this arrangement, the operating wires and the optical fiber bundles passing through the ring assembly will not be damaged by the rivets 20.

In the embodiment of FIG. 9, it is interesting to note that the punch 45 is disposed inwardly of the arcuate members 12A and 12B. In this embodiment, the shape and size of the support base 40 can be selected regardless of the arcuate members 12A and 12B.

Figure 10:
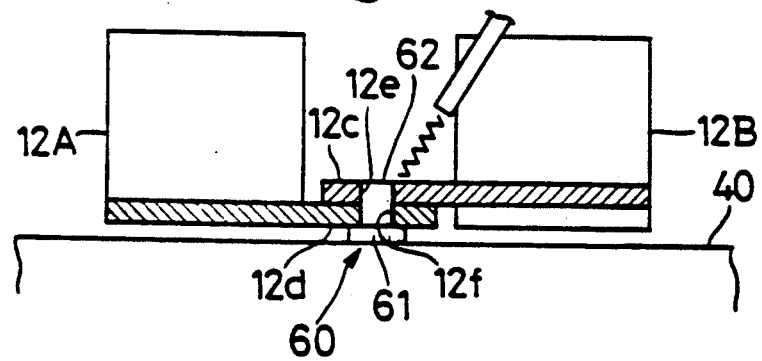

In an embodiment shown in FIG. 10, instead of the rivet, a connecting element 60 having a head 61 and a stem 62 is used to connect the arcuate members 12A and 12B together. In this case, as in FIG. 9, the inner sides of the arcuate members 12A and 12B are directed upwardly, and the head 61 of the connecting element 60 is held against the support base 40. Then, the distal end of the stem 62 is welded to the peripheral edge of the inner end of the through hole 12e by a laser beam. In this embodiment, also, the connecting element 60 is fixed to the first connecting portion 12c and will not axially move relative thereto, and the distal end face of the stem 62 lies substantially flush with the inner surface of the first connecting portion 12c, and is not projected inwardly from this inner surface. With this arrangement, the connecting elements 60 will not damage the operating wires and the optical fiber bundles.

Figure 11:
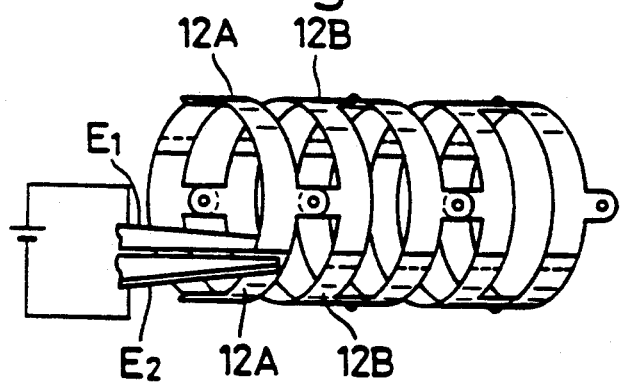
FIG. 11 is a perspective view showing a modified step of fixing the mating arcuate members of the pair of arcuate assemblies at their ends.

FIG. 11 shows a modified method of connecting the ends of the corresponding pair of arcuate members when forming the ring assembly by the pair of arcuate assemblies. This will now be described, for example, with respect to the arcuate members 12A and 12A. The mating end portions of the corresponding pair of arcuate members 12A and 12A are caused to overlap each other, and the overlapping end portions are held between two electrodes E1 and E2, and are spot-welded together. In this case, of course, it is necessary that the arcuate member should be arcuately extended over an angle greater than 180° by an amount corresponding to the overlapping portion thereof. In this embodiment, although the spot-welding is most preferred from the viewpoint of operability, the overlapping ends of the arcuate member 12A and 12A may be brazed or bonded together.

Figure 12:
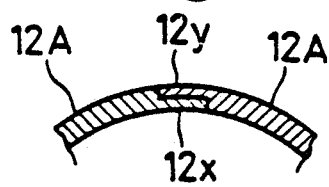
FIGS. 12 to 14 are fragmentary cross-sectional views respectively showing modified steps of fixing the mating arcuate members of the pair of arcuate assemblies at their ends.

FIG. 12 shows a modified form of the invention in which there is provided means for preventing the overlapping end portions of the arcuate members from being increased in thickness. More specifically, one of the corresponding pair of the arcuate members 12A is notched at the outer surface of its end portion 12x to reduce the thickness of the end portion 12x to a half of the thickness of the other portion of the arcuate member 12A. The other arcuate members 12A is notched at the inner surface of its end portion 12y to reduce the thickness of the end portion 12y to a half of the thickness of the other portion of the arcuate member 12A. The end portions 12x and 12y are fitted relative to each other, and are fixed together by spot-welding or the like, thereby forming the joint ring 12. In this embodiment, any projection resulting from the overlapping of the pair of arcuate members 12A and 12A is not formed at either of the inner and outer peripheral surfaces of the joint ring 12.

Figure 13:
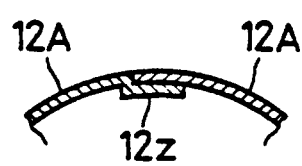

In an embodiment shown in FIG. 13, the end portion 12z of one of the corresponding pair of arcuate members 12A and 12A is offset inwardly by an amount corresponding to the thickness of the arcuate member 12A. The end portion of the other arcuate member 12A is fitted in the end portion 12z, and these two end portions are fixed together by spot-welding or the like, thereby forming the joint ring 12. In this embodiment, any projection resulting from the overlapping of the pair of arcuate members 12A and 12A is not formed at the outer peripheral surface of the joint ring 12.

Figure 14:
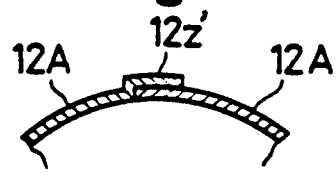

In an embodiment shown in FIG. 14, the end portion 12z' of one of the corresponding pair of arcuate members 12A and 12A is offset outwardly by an amount corresponding to the thickness of the arcuate member 12A. The end portion of the other arcuate member 12A is fitted in the end portion 12z', and these two end portions are fixed together by spot-welding or the like, thereby forming the joint ring 12. In this embodiment, any projection resulting from the overlapping of the pair of arcuate members 12A and 12A is not formed at the inner peripheral surface of the joint ring 12.

Figure 15:
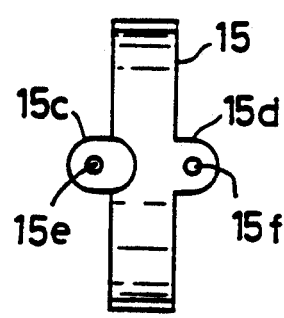
FIG. 15 is a side-elevational view of a modified arcuate member.

The present invention can be applied to the type of bending device in which one or two operating wires are used so as to bend the bending device in one or two directions. In this case, as shown in FIG. 15, each arcuate member 15 of the joint ring has one first connecting portion 15c and one second connecting portion 15d which are projecting respectively in opposite directions along the direction of the width thereof. The first and second connecting portions 15c and 15d are disposed in registry with each other in the direction of the width of the arcuate member 15. Through holes 15e and 15f are formed through the connecting portions 15c and 15d, respectively.

The present invention is not restricted to the above embodiments, and various modifications can be made without departing from the spirits of the invention.

For example, each of the joint rings may be composed of more than two arcuate members, in which case the ring assembly is formed by joining more than two arcuate assemblies together.

Each of the joint rings may have an oval shape or an elliptical shape.

The bending device of this invention can be applied to a surgical catheter.

What is claimed is:

1. A method of producing a bending device comprising an elongated ring assembly and operating wire means for bending said ring assembly, said ring assembly comprising a row of joint rings, and connecting elements pivotally connecting adjacent ones of said joint rings, a distal end of said operating wire means being substantially fixed to a front end of said ring assembly, a proximal end of said operating wire means being adapted to receive an operating force, said method comprising the steps of:
   (a) providing a plurality of elongated arcuate assemblies each separated from the other, each of said arcuate assemblies being formed by pivotally connecting a row of arcuate members to one another by said connecting elements, said arcuate assembly extending in a direction of the widths of said arcuate members;
   (b) connecting adjacent arcuate members to each other at intermediate portions thereof so that said adjacent arcuate members are pivotally movable relative to each other about an axis perpendicular to the direction of the widths of said arcuate members; and
   (c) connecting said plurality of arcuate assemblies together in such a manner that ends of corresponding ones of said arcuate members of said arcuate assemblies are fixed together to form said row of joint rings, thereby forming said ring assembly.

2. A method according to claim 1, in which before forming said ring assembly, guide members for passing said wire operating means therethrough are fixedly secured to said arcuate members.

3. A method according to claim 1, in which each of said arcuate members has a first connecting portion and a second connecting portions which are provided respectively at opposite sides of said arcuate member and are spaced from each other in the direction of the width of said arcuate member, a through hole being formed through each of said first and second connecting portions, each of said connecting element having a head and a stem, and the step of pivotally connecting said arcuate members comprising overlapping said first connecting portion of any one of said arcuate members relative to said second connecting portion of its adjacent arcuate member in such a manner that said first connecting portion is disposed inwardly of said second connecting portion, and subsequently passing said stem of said connecting element through said through holes of said overlapping first and second connecting potions, thereby pivotally connecting said adjacent arcuate members.

4. A method according to claim 3, in which said connecting element comprises a rivet, the step of pivotally connecting said arcuate members comprising passing said stem of said rivet through said through holes of said overlapping first and second connecting portions of any two adjacent ones of said arcuate members in such a manner that said head of said rivet is disposed outside of said arcuate members, holding said head of said rivet against a support bed, and subsequently moving a punch against a distal end of said stem of said rivet to crush said distal end, thereby pivotally connecting said two adjacent arcuate members.

5. A method according to claim 4, in which said stem of said rivet has a greater-diameter portion close to said head and a smaller-diameter portion close to the distal end of said stem, a shoulder being formed between said greater-diameter portion and said smaller-diameter portion, said first connecting portion being held between the crushed distal end of said stem and said shoulder, so that said rivet is fixed to said first connecting portion against axial movement relative thereto, and said second connecting portion being pivotally movable relative to said rivet.

6. A method according to claim 5, in which said through hole formed through said first connecting portion is enlarged at its one end, opening to the inner surface of said first connecting portion, to form a counterbore in which the crushed distal end of said stem of said rivet is received.

7. A method according to claim 3, in which the step of pivotally connecting said arcuate members comprising passing said stem of said connecting element through said through holes of said overlapping first and second connecting portions of any two adjacent ones of said arcuate members in such a manner that said head of said connecting element is disposed outside of said arcuate members, and welding the distal end of said stem to said first connecting portion disposed inwardly of said second connecting portion, so that said connecting element is fixed to said first connecting portion against axial movement relative thereto, and said second connecting portion being pivotally movable relative to said connecting element.

8. A method according to claim 3, in which each of said arcuate members is arcuately extended over an angle of generally 180°, said ring assembly being formed by a pair of said arcuate assemblies, and each of said joint rings constituted by a pair of said arcuate members having a pair of said first connecting portions disposed in diametrically-opposite relation to each other and a pair of second connecting portions disposed in diametrically-opposite relation to each other.

9. A method according to claim 8, in which said operating wire means comprises four operating wires, said first and second connecting portions of each of said arcuate members being circumferentially spaced substantially 90° from opposite ends of said arcuate member, respectively.

10. A method according to claim 8, in which said operating wire means comprises not more than two operating wires, each of said arcuate members having said first and second connecting portions disposed in registry with each other in the direction of the width of said arcuate member.

11. A method according to claim 1, in which the step of fixing the ends of the corresponding arcuate members together comprising abutting said ends of any two of said corresponding arcuate members against each other, and subsequently fixing said abutting ends together.

12. A method according to claim 1, in which the step of fixing the ends of the corresponding arcuate members together comprising causing said ends of any two of said corresponding arcuate members to overlap each other, and subsequently fixing said overlapping ends together.

13. A method according to claim 12, in which the step of fixing the ends of the corresponding arcuate members together comprising notching the inner surface of the end portion of one of any two of the corresponding arcuate members to reduce the thickness of said end portion to a half of the thickness of the other portion of said one arcuate member; notching the outer surface of the end portion of the other of said two corresponding arcuate members to reduce the thickness of said end portion to a half of the thickness of the other portion of said other arcuate member; causing said notched end portions of said two corresponding arcuate members to overlap each other; and subsequently fixing said overlapping end portions together.

14. A method according to claim 12, in which the step of fixing the ends of the corresponding arcuate members together comprising inwardly offsetting one end portion of one of any two of the corresponding arcuate members by an amount corresponding to the thickness of said arcuate member; causing the other end portion of the other of said two corresponding arcuate members to overlap the outer surface of said offset end portion of said one arcuate member; and subsequently fixing said overlapping end portions together.

15. A method according to claim 12, in which the step of fixing the ends of the corresponding arcuate members together comprising outwardly offsetting one end portion of one of any two of the corresponding arcuate members by an amount corresponding to the thickness of said arcuate member; causing the other end portion of the other of said two corresponding arcuate members to overlap the inner surface of said offset end portion; and subsequently fixing said overlapping end portions together.

* * * * *